(12) United States Patent
Romero

(10) Patent No.: US 7,674,484 B2
(45) Date of Patent: Mar. 9, 2010

(54) DIETARY SUPPLEMENT INCLUDING HE SHOU WU, PARASITIC LORANTHUS AND GREEN TEA TO PROMOTE WEIGHT LOSS

(75) Inventor: Timothy Romero, Sarasota, FL (US)

(73) Assignee: Integrity Nutraceuticals International, Sarasota, FL (US)

( * ) Notice: Subject to any disclaimer, the term of this patent is extended or adjusted under 35 U.S.C. 154(b) by 0 days.

(21) Appl. No.: 11/405,749

(22) Filed: Apr. 18, 2006

(65) Prior Publication Data

US 2006/0233828 A1 Oct. 19, 2006

Related U.S. Application Data

(60) Provisional application No. 60/594,545, filed on Apr. 18, 2005.

(51) Int. Cl.
*A61K 36/82* (2006.01)
*A61K 36/00* (2006.01)

(52) U.S. Cl. ........................ 424/729; 424/725

(58) Field of Classification Search ........................ None
See application file for complete search history.

(56) References Cited

U.S. PATENT DOCUMENTS

| 5,612,039 | A | 3/1997 | Policappelli et al. |
|---|---|---|---|
| 5,770,207 | A | 6/1998 | Bewicke |
| 6,241,987 | B1 | 6/2001 | Lam |
| 6,368,617 | B1 | 4/2002 | Hastings et al. |
| 2005/0130933 | A1* | 6/2005 | Jacobs et al. ................. 514/54 |

FOREIGN PATENT DOCUMENTS

| CN | 1108066 | 9/1995 |
|---|---|---|
| CN | 1370589 | 9/2002 |
| CN | 1398527 | 2/2003 |
| CN | 1575809 | 2/2005 |
| CN | 1608523 | 4/2005 |
| WO | WO-2004002503 | 1/2004 |

OTHER PUBLICATIONS

Tian et al.; Weight Reduction by Chinese Medicinal Herbs may be Related to Inhibition of Fatty Acid Synthase.: Life Sciences volime 74, issue 19, Mar. 2004: .: (Available online Jan. 27, 2004) pp. 2389-2399.*
Weight reduction by Cinese medicinal herbs may be related to nhibition of fatty acid synthase.

* cited by examiner

*Primary Examiner*—Patricia Leith
*Assistant Examiner*—Melenie McCormick
(74) *Attorney, Agent, or Firm*—Gifford, Krass, Sprinkle, Anderson & Citkowski, P.C.

(57) ABSTRACT

A novel dietary supplement composition that serves to inhibit FAS for the purpose of controlling body weight and body fat levels. Administration of the composition, particularly to individuals with impaired glucose tolerance, may have the effect of restoring optimal glucose functioning, therefore lessening the likelihood of adipose storage and leading to a reduction in body fat and weight. The supplement may comprise He Shou Wu, parasitic loranthus and green tea. A composition of the dietary supplement, in orally taken capsule form, may include: (a) about 500 mg of an 1:1:1 ratio extract of He Shou Wu, parasitic loranthus and green tea; (b) about 200 mg Caffeine Anhydrous; (c) about 250 mg Cinnulin PF; (d) about 100 mg Evodia Rutaecarpa; (e) about 500 mg tyrosine; and (f) about 100 mg 7-keto DHEA. The supplement may also be administered as a tablet, powdered beverage, bar, gel or drink.

20 Claims, 1 Drawing Sheet

DIETARY SUPPLEMENT INCLUDING HE SHOU WU, PARASITIC LORANTHUS AND GREEN TEA TO PROMOTE WEIGHT LOSS

CROSS REFERENCE TO RELATED APPLICATION

The present application claims priority from U.S. Provisional Application No. 60/594,545 filed on Apr. 18, 2005, the disclosure of which is incorporated in its entirety herein by reference.

BACKGROUND OF THE INVENTION

1. Field of the Invention

The present invention is directed to dietary supplements comprising extracts of He Shou Wu, parasitic loranthus and green tea, or derivatives of the extracts thereof, and to methods of using these dietary supplements to promote weight loss, both in humans and animals.

2. Reference to Related Art

The science of obesity and Type II diabetes involve highly complex systems in human physiology. Both diseases may be approaching epidemic status in the United States. The increased incidence of these conditions has been attributed to diets characterized by high fat intake and repeated ingestion of refined foods and sugars, coupled with low fiber and vegetable intake. Excess amounts of carbohydrate and protein can convert to fatty acids.

Fatty acids are saturated aliphatic monocarboxylic acids that naturally occur in the form of esters in fats, waxes, and essential oils and are stored in the body as triacylglycerols. Triacylglycerols form unstable micelles that coalesce within adipocytes forming a lipid that is stored as a reserve source of energy. The synthesis of fatty acids in humans primarily occurs in the liver and lactating mammary glands, as well as adipose tissue and the kidney.

The first step in fatty acid synthesis is the conversion of acetyl-CoA to malonyl-CoA. This conversion of acetyl-CoA to malonyl-CoA is mediated by an enzyme known as acetyl-CoA carboxylase (ACC). The synthesis of fatty acids from acetyl-CoA and malonyl-CoA is carried out by the enzymatic process of fatty acid synthase (FAS).

The active enzyme of FAS is a dimer of identical subunits. FAS does, however, have multiple enzymatic functions carrying out a variety of reactions in fatty acid synthesis. Some regulators of FAS include insulin and glucose, both of which stimulate the action of FAS. The inverse is true of glucagon and starvation whereby the enzymes actions are inhibited. Glucagon and epinephrine lead to an inhibition of ACC thus inhibiting fatty acid synthesis. Long chain fatty acids also inhibit FAS.

The primary fatty acid synthesized by FAS is palmitate. Thereafter, palmitate is released from the enzyme and can then undergo separate elongation and/or unsaturation to yield other fatty acid molecules. If FAS is inhibited, the body cannot form fatty acids for storage, hence fat accumulation is inhibited. When this occurs, other physiology is altered as well. Aside from fatty acid synthesis, FAS exerts numerous indirect properties particularly on hypothalamic neurons having a great deal of impact on satiety systems.

Studies on FAS inhibitors show increases in neuropeptide mRNA, but the exact mechanism is unknown. This action is similar to the action of leptin, both increase malonyl-CoA levels, however with leptin a "resistance" is built up. The end result of FAS inhibition appears to be a significant reduction in feeding behavior through the modulation of various hypothalamic neuronal pathways.

A few FAS inhibitors have been reported in previous studies as a therapeutic treatment of obesity. One is cerulenin, an unstable and toxic compound from microbes (Omura, 1976), and the other is C75, a synthetic derivative of cerulenin apparently void of toxicity (Kuhajda et al., 2000). A few trials have also looked at FAS as a therapy to induce weight reduction with success. For example, T. Loftus et al. (2000) reported that the treatment of mice with FAS inhibitors led to inhibition of feeding and dramatic weight loss. Therefore, FAS may play an important role in the regulation of feeding and may be a potential target for the treatment of adiposity through dual, yet synergistic mechanisms.

He Shou Wu (see also, Tuber Fleeceflower, *Polygonum multiflorum* or Polygoacetophenoside) is an herb used in Chinese medicine, and is produced in all parts of China. More specifically, He Shou Wu is the root of *polygonum multiflorum* Thunb (pharmaceutical name Radix Polygoni Multiflori). The related plant is called ye jiao teng, which literally means "vines that tangle at night". He Shou Wu is harvested during fall and winter after the leaves of the plant become wilted.

In harvesting, the plant root tuber is dug up, washed clean, sliced and dried. This basic cleaning and drying process yields "unprepared" fleeceflower root. The unprepared fleeceflower root, mixed with black soybean milk, may be steamed and dried alternately and repeatedly until the root becomes black, and a "prepared" fleeceflower root is obtained. The prepared root is bitter, sweet and astringent in flavor, slightly warming in property, acting on the liver and kidney channels. As such, the prepared root may have the effect of replenishing the vital essence and blood, curing malaria, clearing away toxins, moistening the intestines and relieving constipation.

He Shou Wu is found in formulas and tonics. It has recently been popularized by its aid in re-growing hair, keeping hair from turning grey prematurely, and keeping it healthy. This is due to the herb's ability to nourish and replenish blood and nourish the kidneys that in turn promotes healthy growth of hair. Other traditional uses include use against hair loss, dizziness, blurred vision, spermatorrhea, deficiency of vital essence, deficiency of blood, lassitude of the loins and legs, deficiency of the liver-yin and kidney-yin accompanied with hyperactivity of the liver-yang with manifestations of dizziness, blurred vision and numbness of the extremities, chronic malaria due to deficiency of both Qi and blood, sores, swelling, scrofula, constipation due to deficiency of the blood and dryness of the bowels.

Green tea is a compound known for its effect on body weight and as a therapeutic target for adiposity. However, the vast majority of research on green tea focuses on a compound known as EGCG. Dulloo et al. have studied the effects of green tea and shown it to both increase energy expenditure and lead to a decrease in weight circumference. Additionally, green tea is known to have a host of other benefits. Never before has green tea been looked at in respect to having FAS inhibitory properties, nor effects on satiety.

In a recent study, Tian et al. found that Tuber Fleeceflower (*Polygonum multiflorum*) (see also, He Shou Wu or Polygoacetophenoside), green tea (see also, *Camellia sinensis* or Epigallocatechin gallate (EGCG)) and parasitic loranthus (*Loranthus parasiticus*) were shown to have a significant FAS inhibiting effects similar to the C75 FAS inhibitor. See Tian W X, et al., Weight reduction by Chinese medicinal herbs may be related to inhibition of fatty acid synthase. *Life Sci*

2004; 74: 2389-99 (2004). In Tian, reversible inhibition and irreversible inhibition was assessed on FAS by ethanol and water extracts of various Chinese herbs. Of the numerous herbs that were screened in the process, these three herbs seemed to stand out with great potential, all showing at or near 100% inhibition of the fat storing enzyme.

In addition to Tian, Chinese Publ. No. CN1088053 disclosed a life-prolonging health tea that includes a mix of prepared *Polygonum multiflorum* with black tea, green tea or scented tea in certain proportions. The tea is described as having an effect on insomnia, blood deficiency, constipation and other diseases.

Chinese Publ. No. CN1108066 disclosed a health-care beverage for prevention against x-rays. The drink includes green tea filtrate, filtrate of *polygonum* multiflorum and other ingredients and is described as having an effect on relieving mental uneasiness and resolving phlegm.

Chinese Publ. No. CN1370589 disclosed a sobering-up toxin-eliminating tea and its preparation. Specifically the tea is disclosed as including green tea, mint, galangal fruit, parasitic loranthus, clove, licorice and other ingredients and is described as functioning to detoxify the user.

Chinese Publ. No. CN1398527 disclosed a golden transparent medicated preserved egg and its preservation process that includes fleeceflower root and parasitic loranthus.

Chinese Publ. No. CN1575809 disclosed an antilipemic Chinese herbal medicine that includes 20-30% raw fleeceflower, 10-20% prepared fleeceflower, 10-20% parasitic loranthus and other ingredients.

Chinese Publ. No. CN1608523 disclosed the production process of fleeceflower root tea beverage that includes 3-4% green tea, 0.4-0.6% fleeceflower root and other ingredients.

Finally, International Publication No. WO 2004/002503 to Clavey disclosed compositions and methods for treating gynaecological disorder.

SUMMARY OF THE INVENTION

Disclosed herein is: (a) a dietary supplement comprising substantially equal amounts of an extract of He Shou Wu, parasitic loranthus and green tea, or a derivative of the extract thereof and (b) methods of losing weight and reducing body fat comprising administration of said dietary supplement. The novel dietary supplement composition serves to inhibit FAS for the purpose of controlling body weight and body fat levels. Administration of the composition, particularly to individuals with impaired glucose tolerance, may have the effect of restoring optimal glucose functioning, therefore lessening the likelihood of adipose storage and leading to a reduction in body fat and weight.

In one embodiment, the supplement may comprise He Shou Wu, parasitic loranthus and green tea. A composition of the dietary supplement, in orally taken capsule form, may include: (a) about 500 mg of a composition formed from extract of a He Shou Wu, parasitic loranthus and green tea prepared using an initial 1:1:1 ratio preparation of the three constituent ingredients; (b) about 200 mg Caffeine Anhydrous; (c) about 250 mg Cinnulin PF; (d) about 100 mg Evodia Rutaecarpa; (e) about 500 mg tyrosine; and (f) about 100 mg 7-keto DHEA. The supplement may also be administered as a tablet, powdered beverage, bar, gel or drink.

A method for preparing the 500 mg of a composition mentioned above may include a first step wherein a user collects predetermined amounts of He Shou Wu, parasitic loranthus and green tea (leaves and/or whole plants). These components may then be combined, in equal parts by weight at a 1:1:1 ratio. For example, in one embodiment the amounts of the initial components that may be used are between 1-25 kg of He Shou Wu, 1-25 kg of parasitic loranthus and 1-25 kg of green tea. The combined components may next undergo an extraction process using a 50% ethanol solution and known extraction techniques. This extraction process may then be repeated two more times. In the next step, the resulting extract may be filtered and any impurities and residue removed. Once filtered, the extract may be chilled and processed through a solvent recovery operation. The extract may then be spray dried to yield a powder. This powder may then be shifted and packed to yield the resulting composition.

As will be further detailed hereinbelow, the present invention provides a method and a dietary supplement that will promote weight loss and body fat reduction when administered at normal physiological concentrations.

Other advantages and features of the invention will become apparent from the following detailed description, and from the claims.

DESCRIPTION OF THE DRAWINGS

Reference will now be made to the associated drawings, wherein like reference numerals refer to like parts throughout, and wherein.

DETAILED DESCRIPTION

Figure 1:
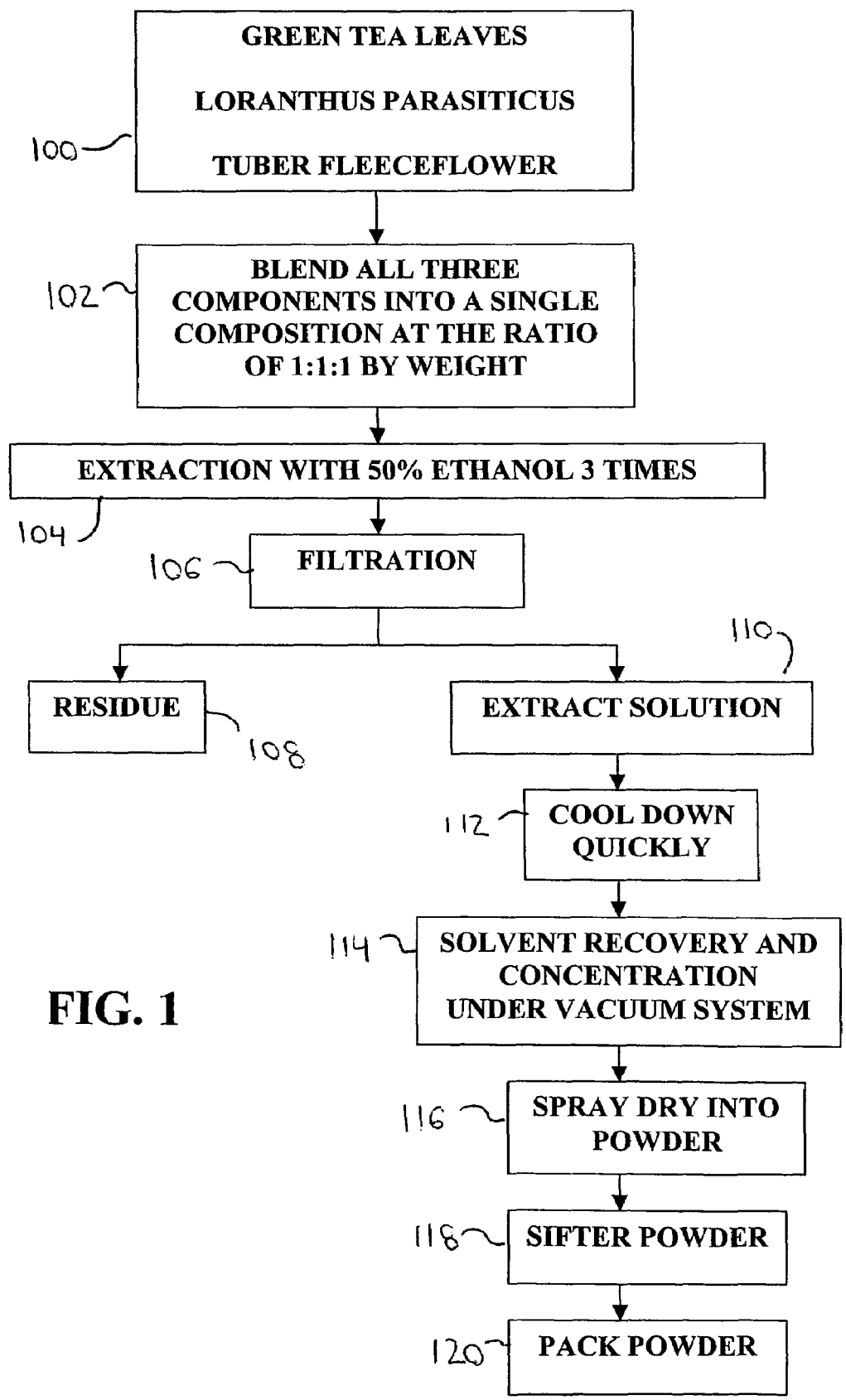
FIG. 1 is a schematic view of a method for producing a dietary supplement in accordance with the present invention.

A body fat reduction and weight loss dietary supplement and extraction method may include He Shou Wu, parasitic loranthus (*Loranthus parasiticus*) and green tea (epigallocatechin-3-gallate—EGCG), and extracts thereof or a derivative of the extracts thereof. A formulation of the body fat reduction and weight loss dietary supplements may include about 1 mg to about 10,000 mg of He Shou Wu, 1 mg to about 10,000 mg of parasitic loranthus and 1 mg to about 10,000 mg of green tea extract, or like amounts of He Shou Wu, parasitic loranthus and green tea extract derivative per gram of dietary supplement. A daily dosage of the body fat reduction and weight loss dietary supplement may include about 10 mg to about 10,000 mg of He Shou Wu, 10 mg to about 10,000 mg of parasitic loranthus and 10 mg to about 10,000 mg of green tea extract, or like amounts of He Shou Wu, parasitic loranthus and green tea extract derivative. The body fat reduction and weight loss dietary supplement may also be administered in an amount of from about 100 mg to about 500 g per day.

More specifically, a dietary supplement may include an orally ingestible form, such as a capsule or tablet, that includes a combination of He Shou Wu, parasitic loranthus and green tea extract in a ration of 1:1:1 by weight. Other additives such as a further amount of Green Tea, TTA (TetradecylThioacetic Acid), Tyosine, Guggulsterones, Caffeine Anhydrous, Synephrine HCL, Yohimbine HCL, Evodia Rutaecarpa, Raspberry Ketone, Coleus Forshkohlii, Cinnulin PF, and 7-keto DHEA may also be secondarily included in the capsule or tablet. As mentioned, the dietary supplement composition may be put into capsules using known technology, such that the recommended daily dose for an adult would be one to three capsules.

Referring now of FIG. 1, there is shown a method for the production of a composition of He Shou Wu, parasitic loranthus and green tea extract.

As mentioned above, He Shou Wu has a common name in English-speaking countries as Fleeceflower Root and is known in China as He Shou Wu, Shouwu, or Chishouwu. He Shou Wu may be harvested in autumn and winter when leaves wither, washed clean, and the large ones cut into pieces, and then dried to produce a dried He Shou Wu. He Shou Wu can also be prepared by steaming (e.g., for 3 hr) to produce a steamed He Shou Wu, optionally in the presence of wine to produce the so-called wine-processed He Shou Wu. The slices or pieces of He Shou Wu may be mixed thoroughly with black bean juice and stewed in a suitable non-ferrous container until the juice is exhausted. The mixture is dried to solidify and then cut into slices to produce the so-called prepared He Shou Wu.

Crude He Shou Wu and prepared He Shou Wu may differ in the composition. It is known that all kinds of He Shou Wu contain free phosphatidylcholine (lecithin), phosphatidylinositol, phosphatidylcholine, phosphatidylethanolamine (cephalin), N-free phosphatidylethanolamine and sphingolipids. Crude He Shou Wu usually contains 3.7% phospholipids, and higher than processed He Shou Wu. He Shou Wu also contains emodins such as anthraquinones or anthrones which mainly form glycoside with glucose and rhamnose to form mono- or di-glycoside, chrysophanol, emodin, rhein, chrysophanol ester, and chrysophanin acid anthrone. Processed He Shou Wu has a lower concentration of anthraquinones. He Shou Wu also contains tetrahydroxystilbene glycoside and its analogues, and the processed He Shou Wu has a slightly higher concentration. He Shou Wu is abundant of trace elements, such as calcium, iron, manganese, copper, and zinc at a concentration of about 421 ug/g, ten times higher than most herb. In addition, He Shou Wu has high concentration of starch, soluble amylose, vitamins, amino acids, and coarse fat.

The He Shou Wu used in the composition of the present invention may be obtained from one of many commercially available sources and may be in a prepared or an unprepared form.

Regarding parasitic loranthus, in China, the parasitic loranthus is mainly produced in Guangdong or Guangxi. However, it is readily commercially available on the open market. The herb is harvested in winter to spring of the following year. Remove the thick stem, cut the stem or branch into lengths, dry or steam them before drying and use when raw. Parasitic loranthus has a bitter and sweet flavor, mild in nature, it is related to the liver and kidney channels. Further, parasitic loranthus is generally thought to strengthen bones and muscles.

As mentioned above, green tea is a compound known for its effect on body weight and as a therapeutic target for adiposity. However, the vast majority of research on green tea focuses on a compound known as EGCG. Additionally, green tea is known to have a host of other benefits.

In one embodiment, the composition for the dietary supplement may be produced by, as a first step 100, a user obtained predetermined amounts of He Shou Wu, parasitic loranthus and green tea. These components may then be combined, in a next step 102, by weight at a 1:1:1 ratio. For example, in one embodiment the amounts of the initial components that may be used are between 1-25 kg of He Shou Wu, 1-25 kg of parasitic loranthus and 1-25 kg of green tea. The green tea used may be green tea leaves or whole plants. In a next step 104, the combined components may undergo extraction using a 50% ethanol solution and known extraction techniques. This extraction process may then be repeated two more times. In a next step 106, the resulting extract may be filtered and, in a further step 108, 110, any impurities and residue may be removed.

Once filtered, in a next step 112 the extract may be chilled (in an ice bath or the like) and, in a further step 114, may be processed through a solvent recovery operation. Next 116, the extract may be spray dried to yield a powder. This powder may then be shifted (step 118) and packed (step 120) to yield the resulting composition.

Example 1

In one embodiment, shown below, the composition identified as I-FAS50(3)tm is a 500 mg powder prepared in accord with the present invention and, more specifically, the method set forth above for the combination of a 1:1:1 ratio of He Shou Wu, parasitic loranthus and green tea. Other additives, also identified, may be incorporated with the composition into a capsule using known techniques. The capsule should be used in conjunction with an appropriate food reduction and exercise program. The suggested intake should be taken 1 hour before meals with water based on the weight information.

| Ingredient | Spec | Amount |
| --- | --- | --- |
| Green Tea | 45% EGCG | 300 mg |
| TTA | 99% | 1000 mg |
| Tyrosine | Premium Processing | 500 mg |
| Guggulsterones | 95% | 15 mg |
| Caffeine Anhydrous | 99% | 200 mg |
| I-FAS50(3)tm | | 500 mg |

Example 2

In another embodiment, shown below, the composition identified as I-FAS50(3)tm is a 500 mg powder prepared in accord with the present invention and, more specifically, the method set forth above for the combination of a 1:1:1 ratio of He Shou Wu, parasitic loranthus and green tea. Other additives, also identified, may be incorporated with the composition into a capsule using known techniques. The capsule should be used in conjunction with an appropriate food reduction and exercise program. The suggested intake should be taken 1 hour before meals with water based on the weight information.

| Ingredient | Spec | Amount |
| --- | --- | --- |
| Synephrine HCL | 95% | 20 mg |
| Yohimbine HCL | 99% | 5 mg |
| Guggulsterones | 95% | 15 mg |
| Evodia Rutaecarpa | 10% Evodiamine | 100 mg |
| Caffeine Anhydrous | 99% | 200 mg |
| I-FAS50(3)tm | | 500 mg |
| Green Tea | 45% EGCG | 300 mg |

Example 3

In another embodiment, shown below, the composition identified as I-FAS50(3)tm is a 500 mg powder prepared in accord with the present invention and, more specifically, the method set forth above for the combination of a 1:1:1 ratio of He Shou Wu, parasitic loranthus and green tea. Other additives, also identified, may be incorporated with the composition into a capsule using known techniques. The capsule should be used in conjunction with an appropriate food reduction and exercise program. The suggested intake should be taken 1 hour before meals with water based on the weight information.

| Ingredient | Spec | Amount |
| --- | --- | --- |
| Raspberry Ketone | 99% | 100 mg |
| I-FAS50(3)tm | | 500 mg |
| Green Tea | 45% EGCG | 200 mg |
| Caffeine Anhydrous | 99% | 200 mg |
| Coleus Forshkohlii | 10% | 200 mg |

Example 4

In another embodiment, shown below, the composition identified as I-FAS50(3)tm is a 500 mg powder prepared in accord with the present invention and, more specifically, the method set forth above for the combination of a 1:1:1 ratio of He Shou Wu, parasitic loranthus and green tea. Other additives, also identified, may be incorporated with the composition into a capsule using known techniques. The capsule should be used in conjunction with an appropriate food reduction and exercise program. The suggested intake should be taken 1 hour before meals with water based on the weight information.

| Ingredient | Spec | Amount |
| --- | --- | --- |
| I-FAS50(3)tm | | 500 mg |
| Caffeine Anhydrous | 99% | 200 mg |
| Cinnulin PF | 6% | 250 mg |
| Evodia Rutaecarpa | 10% Evodiamine | 100 mg |
| Tyrosine | Premium Processing | 500 mg |
| 7-keto DHEA | 95% | 100 mg |

Thus, there has been disclosed a dietary supplement comprising a composition of a 1:1:1 ratio of He Shou Wu, parasitic loranthus and green tea or a derivative of the extract thereof. It will be readily apparent to those skilled in the art that various changes and modifications of an obvious nature may be made without departing from the spirit of the invention, and all such changes and modifications are considered to fall within the scope of the invention as defined by the appended claims.

I claim:

1. A dietary supplement comprising: He Shou Wu, parasitic loranthus and green tea wherein the He Shou Wu, parasitic loranthus and green tea are present in a ratio of 1:1:1 by weight.

2. The dietary supplement of claim 1, further comprising an additive selected front a group consisting of: Epigallocatechin gallate, Tetradecyl Thioacetic Acid, Tyosine, Guggulsterones, Caffeine Anhydrous, Synephrine HCL, Yohimbine HCL, Evodia Rutaecarpa, Raspberry Ketone, Coleus Forshkohlii, Cinnulin PF, and 7-keto dehydroepiandrosterone (DHEA).

3. A dietary supplement comprising the following components:
   a. about 1 to 10,000 mg of He Shou Wu extract;
   b. about 1 to 10,000 mg green tea extract; and
   c. about 1 to 10,000 mg parasitic loranthus extract wherein the He Shou Wu extract, parasitic loranthus extract and green tea extract are present at a ratio of 1:1:1 by weight.

4. The dietary supplement of claim 3, further comprising an additive selected from a group consisting of: Epigallocatechin gallate, Tetradecyl Thioacetic Acid, Tyrosine, Guggulsterones, Caffeine Anhydrous, Synephrine HCL, Yohimbine HCL, Evodia Rutaecarpa, Raspberry Ketone, Coleus Forshkohlii, Cinnulin PF, and 7-keto DHEA.

5. The dietary supplement of claim 3 further comprising about 1 mg to 500 mg of Epigallocatechin gallate.

6. The dietary supplement of claim 3 further comprising about 1 mg to 100 mg of Guggulsterones.

7. The dietary supplement of claim 3 further comprising about 1 mg to 1000 mg of Tyrosine.

8. The dietary supplement of claim 3 further comprising about 1 mg to 2000 mg of Tetradecyl Thioacetic Acid.

9. The dietary supplement of claim 3 further comprising about 1 mg to 500 mg of Caffeine Anhydrous.

10. The dietary supplement of claim 3 further comprising about 1 mg to 100 mg of Synephrine HCL.

11. The dietary supplement of claim 3 further comprising about 1 mg to 100 mg of Yohimbine HCL.

12. The dietary supplement of claim 3 further comprising about 1 mg to 100 mg of Yohimbine HCL.

13. The dietary supplement of claim 3 further comprising about 1 mg to 500 mg of Evodia Rutaecarpa.

14. The dietary supplement of claim 3 further comprising about 1 mg to 500 mg of Raspberry Ketone.

15. The dietary supplement of claim 3 further comprising about 1 mg to 500 mg of Coleus Forshkohlii.

16. The dietary supplement of claim 3 further comprising about 1 mg to 500 mg of Cinnulin PF.

17. The dietary supplement of claim 3 further comprising about 1 mg to 500 mg of 7-keto DHEA.

18. A method for manufacturing a dietary supplement comprising the steps of:
   providing a predetermined amount of He Shou Wu, parasitic loranthus and green tea;
   mixing in a 1:1:1 ratio by weight the He Shou Wu, parasitic loranthus and green tea to form a composition;
   processing the composition with a 50% ethanol solution to obtain a composition extract;
   filtering the composition extract;
   chilling the filtered extract;
   processing the filtered extract to recover any remaining solvent; and
   drying the processed filtered extract to yield a powder.

19. The method of claim 18, further the step of packing the powder into an orally ingestible form.

20. The method of claim 19, further the step of packing the orally ingestible form with an additive selected from a group consisting of: Epigallocatechin gallate, Tetradecyl Thioacetic Acid, Tyrosine, Guggulsterones, Caffeine Anhydrous, Synephrine HCL, Yohimbine HCL, Evodia Rutaecarpa, Raspberry Ketone, Coleus Forshkohlii, Cinnulin PF, and 7-keto DHEA.

* * * * *

UNITED STATES PATENT AND TRADEMARK OFFICE
CERTIFICATE OF CORRECTION

PATENT NO.           : 7,674,484 B2                                                        Page 1 of 1
APPLICATION NO.  : 11/405749
DATED                   : March 9, 2010
INVENTOR(S)         : Tim Romero It is certified that error appears in the above-identified patent and that said Letters Patent is hereby corrected as shown below:

Column 7, line 50 - delete "front" and insert --from--

Signed and Sealed this

Twenty-eighth Day of September, 2010

David J. Kappos
*Director of the United States Patent and Trademark Office*